United States Patent
Tazoe et al.

(10) Patent No.: US 6,448,029 B1
(45) Date of Patent: *Sep. 10, 2002

(54) METHOD AND REAGENT FOR QUANTITATIVE DETERMINATION OF 1,5-ANHYDROGLUCITOL

(75) Inventors: Sakae Tazoe, Fuji; Akira Miike, Shizuoka, both of (JP)

(73) Assignee: Kyowa Medex Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,038

(22) Filed: Aug. 15, 2001

Related U.S. Application Data

(62) Division of application No. 09/456,998, filed on Dec. 7, 1999.

(30) Foreign Application Priority Data

Feb. 18, 1999 (JP) .............................................. 11-039433
Dec. 7, 1999 (JP) .............................................. 10-353586

(51) Int. Cl.[7] .............................. C12Q 1/32; C12Q 1/54; C12Q 1/00; G01N 33/53
(52) U.S. Cl. ............................ 435/26; 435/14; 435/4; 435/975; 435/966; 435/175; 435/183
(58) Field of Search .................. 435/26, 14, 4, 435/975, 966, 175, 183

(56) References Cited

U.S. PATENT DOCUMENTS

| 4,994,377 A | 2/1991 | Nakamura et al. ............. 435/25 |
| 5,871,949 A | 2/1999 | Ebinuma et al. ............... 435/26 |
| 5,916,761 A | 6/1999 | Koga et al. .................... 435/21 |
| 6,153,419 A | 11/2000 | Aisaka et al. .................. 435/26 |
| 6,309,852 B1 * | 10/2001 | Tazoe et al. ................... 435/26 |

FOREIGN PATENT DOCUMENTS

| JP | 64-6756 | 2/1989 |
| JP | 1-320998 | 12/1989 |
| JP | 2-104298 | 4/1990 |
| JP | 3-27299 | 2/1991 |
| JP | 5-76397 | 3/1993 |
| JP | 6-237794 | 8/1994 |
| JP | 8-10776 | 4/1996 |
| JP | 9-234098 | 9/1997 |
| JP | 10-84953 | 4/1998 |
| JP | 10-191998 | 7/1998 |
| JP | 63185397 | 7/1998 |

* cited by examiner

Primary Examiner—Louise N. Leary
(74) Attorney, Agent, or Firm—Fitzpatrick, Cella, Harper & Scinto

(57) ABSTRACT

The present invention provides a simple method for the determination of a specific component, e.g. 1,5-anhydroglucitol (1,5-AG) in a sample containing glucose, and a reagent and a reagent kit useful in the method. In one embodiment, a method for the determination of 1,5-AG is provided which comprises contacting the sample with an enzyme system which converts glucose into fructose-1,6-diphosphate and converts 1,5-AG into 1,5-AG-6-phosphate to form 1,5-AG-6-phosphate, dehydrogenating 1,5-AG-6-phosphate in the sample by the action of 1,5-AG-6-phosphate dehydrogenase in the presence of an oxidized coenzyme, and measuring the amount of the reduced coenzyme formed by the dehydrogenation reaction. A reagent and a reagent kit useful in this method are also provided.

18 Claims, 2 Drawing Sheets

US 6,448,029 B1

METHOD AND REAGENT FOR QUANTITATIVE DETERMINATION OF 1,5-ANHYDROGLUCITOL

This application is a division of application Ser. No. 09/456,998 filed Dec. 7, 1999.

BACKGROUND OF THE INVENTION

The present invention relates to a method for the quantitative determination of a specific component, e.g., 1,5-anhydroglucitol (hereinafter referred to as 1,5-AG) in a sample by utilizing an enzyme reaction. The method involves pretreatment which converts glucose in the sample into another substance. The invention also relates to a reagent and a reagent kit useful in the method.

Biological samples contain glucose, sometimes at very high concentrations compared with analytes, which may reduce the accuracy of assay results for analytes. In such cases, prior to the determination of analytes, glucose in samples is removed therefrom or converted into substances which do not interfere with the determination of analytes.

Previous methods for removing glucose from samples include methods in which glucose is separated by ion exchange column chromatography (Japanese Published Unexamined Patent Applications Nos. 185307/88 and 6756/89). Previous methods for converting glucose in samples into other substances include (1) a method in which glucose is converted into glucose-6-phosphate by a reaction utilizing the action of a phosphorylated enzyme such as glucokinase or hexokinase in the presence of adenosine triphosphate (ATP), and (2) a method in which glucose is converted into gluconolactone by a reaction utilizing the action of oxidase such as glucose oxidase, pyranose oxidase or sorbose oxidase in the presence of oxygen.

Further, various improvements have been made to these methods for the conversion of glucose. For example, modifications of the above method (1) using a phosphorylated enzyme include the following: a method in which glucose is converted into fructose-1,6-diphosphate by the action of phosphohexose isomerase and 6-phosphofructokinase in order to prevent the reconversion of glucose-6-phosphate into glucose by equilibrium reaction (Japanese Published Unexamined Patent Application No. 76397/93); methods using glucose-6-phosphate dehydrogenase in the presence of oxidized coenzymes (Japanese Published Unexamined Patent Applications Nos. 320998/89, 27299/91 and 237794/94); and a method using pyruvate kinase in the presence of adenosine diphosphate (ADP) to prevent the change in concentration of ATP, which decreases in the elimination of glucose, and to keep the ATP concentration constant (Japanese Published Unexamined Patent Application No. 104298/90). Modifications of the above method (2) using oxidase include a method in which a reaction using glucose oxidase is carried out and then the formed hydrogen peroxide is eliminated by the action of catalase (Japanese Published Unexamined Patent Application No. 185397/88).

However, the above methods suffer from the defect that enzyme reaction systems for the determination of analytes may be affected by the substances used for the conversion of glucose into other substances and the substances formed in the conversion system as well as their concentration. For example, when glucose is eliminated by the use of glucokinase or hexokinase (Japanese Published Unexamined Patent Application No. 76397/93), ADP is unfavorably formed in large quantities. Particularly, when a sufficient amount of ATP is supplied in order to completely eliminate glucose, ADP is formed at a concentration which is two times higher than that of glucose. The influence of ADP at such concentration on the reaction systems is not negligible.

1,5-AG is present in biological fluids such as cerebrospinal fluid, blood plasma, serum and urine. The level of 1,5-AG in blood plasma decreases in patients of certain diseases, especially diabetes, and thus 1,5-AG is useful as a diagnostic marker for diabetes. However, the determination of 1,5-AG is very difficult because of the close similarity in structure between 1,5-AG and glucose and the small quantity of 1,5-AG compared with glucose.

It is known that enzymes such as sorbose oxidase, pyranose oxidase, hexokinase, glucokinase and ADP-dependent hexokinase act on 1,5-AG, but these enzymes react also with sugars such as glucose which coexist with 1,5-AG. Therefore, some measures must be taken for removing or eliminating these sugars such as glucose.

Some methods comprising the step of elimination of glucose are known for the 1,5-AG determination in which 1,5-AG is oxidized using the catalytic action of pyranose oxidase or sorbose oxidase and the formed hydrogen peroxide is determined.

Examples of such methods are: (1) methods for 1,5-AG determination which comprise separating glucose in a sample by ion column chromatography, contacting the sample with pyranose oxidase, and determining the formed hydrogen peroxide (Japanese Published Unexamined Patent Applications Nos. 185307/88 and 6756/89); (2) methods for 1,5-AG determination which comprise converting glucose in a sample into a compound which does not react with pyranose oxidase by the action of glucokinase or hexokinase and glucose-6-phosphate dehydrogenase, contacting the sample with pyranose oxidase, and determining the formed hydrogen peroxide (Japanese Published Unexamined Patent Applications Nos. 320998/89 and 27299/91); (3) a method for 1,5-AG determination which comprises converting glucose in a sample into a compound which does not react with pyranose oxidase by the action of glucokinase and pyruvate kinase, contacting the sample with pyranose oxidase, and determining the formed hydrogen peroxide (Japanese Published Unexamined Patent Application No. 104298/90); and (4) a method for 1,5-AG determination which comprises converting glucose in a sample into a compound which does not react with pyranose oxidase by the action of hexokinase, phosphohexose isomerase and 6-phosphofructokinase, contacting the sample with sorbose oxidase or pyranose oxidase, and determining the formed hydrogen peroxide (Japanese Published Unexamined Patent Application No. 76397/93).

However, the above methods (1) using columns are disadvantageous because of their complicatedness in operation, and the above methods (2)–(4) have the disadvantage that hexokinase and glucokinase used in their glucose elimination systems act also on 1,5-AG to form 1,5-AG-6-phosphate, which reduces the accuracy of the assays for 1,5-AG.

Further, some methods comprising the step of elimination of glucose are known for the 1,5-AG determination in which 1,5-AG is phosphorylated using the catalytic action of hexokinase, glucokinase or ADP-dependent hexokinase and the formed substance is determined.

Examples of such methods are: (5) a method for 1,5-AG determination which comprises separating glucose in a sample by ion column chromatography, contacting the sample with hexokinase or glucokinase, and determining the formed ADP (Japanese Published Unexamined Patent Application No. 107796/96); and (6) a method for 1,5-AG determination which comprises converting glucose in a sample into a compound which does not react with ADP-dependent hexokinase by the action of (a) glucose oxidase, or glucose oxidase and catalase, (b) glucose dehydrogenase, or (c) hexokinase or glucokinase, contacting the sample with ADP-dependent hexokinase and 1,5-AG-6-phosphate dehydrogenase, and determining the formed reduced nicotinamide adenine dinucleotide (phosphate) [NAD(P)H] (Japanese Published Unexamined Patent Apllication No. 191998/98).

However, these methods suffer from the following disadvantages. Method (5) requires complicated operations. In method (6), in the case of (a) using glucose oxidase, oxygen supply is a rate-limiting step when glucose is present in a sample at a high concentration; in the case of (b) using glucose dehydrogenase, a system for eliminating NAD(P)H formed from glucose is required; and in the case of (c) using hexokinase or glucokinase, fractional determination can not be carried out because 1,5-AG-6-phosphate dehydrogenase acts on glucose-6-phosphate formed from glucose, and when the method is applied to samples containing a large quantity of glucose such as those from diabetes patients, ADP formed in the reaction system in a large quantity has an unfavorable effect on the accuracy of the assay for 1,5-AG.

Under the circumstances, an object of the present invention is to provide a simple method for the determination of a specific component, e.g. 1,5-AG, in a sample containing glucose, a method for substantially completely eliminating glucose in a sample in the determination of a specific component in the sample, and a reagent and a kit useful in the methods.

SUMMARY OF THE INVENTION

The present invention relates to a method for determining 1,5-AG in a sample containing glucose, which comprises contacting the sample with an enzyme system which converts glucose into fructose-1,6-diphosphate and converts 1,5-AG into 1,5-AG-6-phosphate to form 1,5-AG-6-phosphate, dehydrogenating 1,5-AG-6-phosphate in the sample by the action of 1,5-AG-6-phosphate dehydrogenase in the presence of an oxidized coenzyme, and measuring the amount of the reduced coenzyme formed by the dehydrogenation reaction.

The present invention also relates to a reagent for the determination of 1,5-AG, comprising (a) nucleosidediphosphate (hereinafter referred to as NDP), nucleoside triphosphate (hereinafter referred to as NTP), NDP-dependent hexokinase, phosphohexose isomerase, 6-phosphofructokinase, an oxidized coenzyme and 1,5-AG-6-phosphate dehydrogenase, or (b) one member selected from the group consisting of NTP-dependent hexokinase and NTP-dependent glucokinase, NTP, phosphohexose isomerase, 6-phosphofructokinase, an oxidized coenzyme and 1,5-AG-6-phosphate dehydrogenase.

The present invention further relates to a reagent kit for the determination of 1,5-AG, comprising (a) a reagent comprising NDP, NTP, NDP-dependent hexokinase, phosphohexose isomerase and 6-phosphofructokinase, or (b) a reagent comprising one member selected from the group consisting of NTP-dependent hexokinase and NTP-dependent glucokinase, NTP, phosphohexose isomerase and 6-phosphofructokinase, and a reagent comprising an oxidized coenzyme and 1,5-AG-6-phosphate dehydrogenase.

The present invention further relates to a method for eliminating glucose in a sample, which comprises converting glucose in the sample into fructose-1,6-diphosphate by the action of NDP-dependent hexokinase, phosphohexose isomerase and 6-phosphofructokinase in the presence of NDP and NTP.

The present invention further relates to a reagent for the elimination of glucose, comprising NDP, NTP, NDP-dependent hexokinase, phosphohexose isomerase and 6-phosphofructokinase.

The present invention further relates to a method for determining an analyte in a sample containing glucose, which comprises converting glucose in the sample into fructose-1,6-diphosphate by the action of NDP-dependent hexokinase, phosphohexose isomerase and 6-phosphofructokinase in the presence of NDP and NTP, and determining the analyte in the sample by using a chemical or enzymatic reaction.

The present invention further relates to a reagent for the determination of an analyte, comprising NDP, NTP, NDP-dependent hexokinase, phosphohexose isomerase, 6-phosphofructokinase, and an enzyme acting on the analyte or a substance reacting with the analyte.

The present invention further relates to a reagent kit for the determination of an analyte, comprising a reagent comprising NDP, NTP, NDP-dependent hexokinase, phosphohexose isomerase and 6-phosphofructokinase, and a reagent comprising an enzyme acting on the analyte or a substance reacting with the analyte.

DETAILED DESCRIPTION OF THE INVENTION

Figure 1:
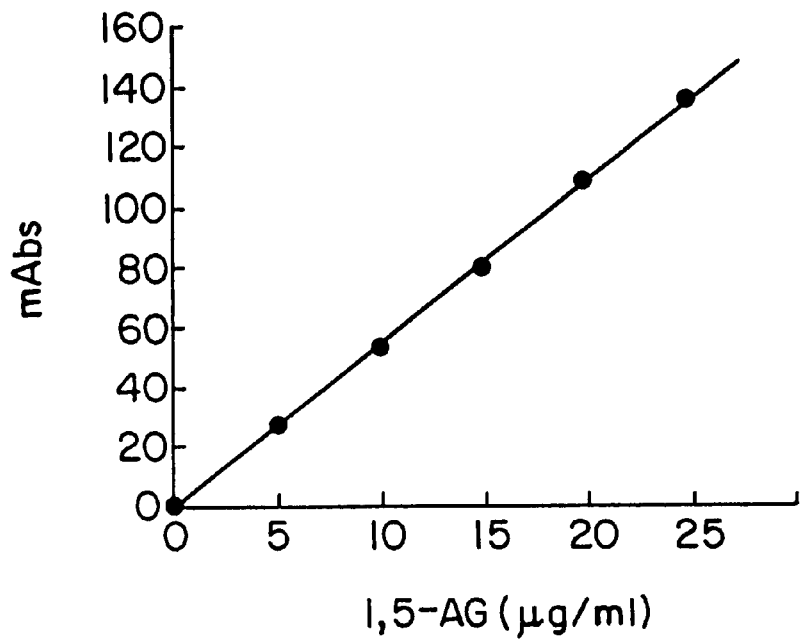
FIG. 1 shows a calibration curve for 1,5-AG. 1,5-AG on the abscissa refers to 1,5-anhydroglucitol and mAbs on the ordinate refers to milli-absorbance.

The present invention is applicable to assays of any samples which may contain glucose, for example, biological samples such as blood, plasma, serum and urine.

In accordance with the present invention, elimination of glucose in samples is carried out by converting glucose into fructose-1,6-diphosphate according to the following reaction formula.

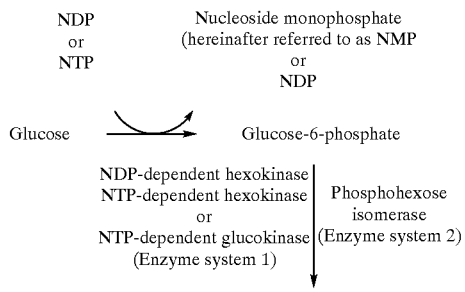

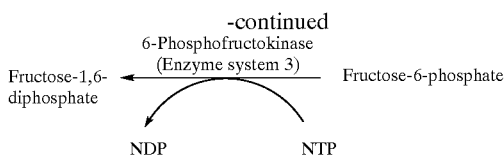

Conversion of glucose into glucose-6-phosphate alone is not sufficient for eliminating glucose because this conversion reaction is reversible and will allow the formed glucose-6-phosphate to be reconverted into glucose. In the above reaction system, glucose in a sample can be completely eliminated by converting glucose into fructose-1,6-diphosphate so as to prevent the reconversion into glucose.

The enzyme system which converts glucose into fructose-1,6-diphosphate comprises an enzyme system for forming glucose-6-phosphate from glucose (hereinafter referred to as enzyme system 1), an enzyme system for forming fructose-6-phosphate from glucose-6-phosphate (hereinafter referred to as enzyme system 2), and an enzyme system for forming fructose-1,6-diphosphate from fructose-6-phosphate (hereinafter referred to as enzyme system 3).

Enzyme system 1 includes the following two systems: (a) in which the enzyme is NDP-dependent hexokinase and the coenzyme is NDP, which is converted into NMP, and (b) in which the enzyme is NTP-dependent hexokinase or NTP-dependent glucokinase and the coenzyme is NTP, which is converted into NDP. In enzyme system 2, the enzyme is phosphohexose isomerase. In enzyme system 3, the enzyme is 6-phosphofructokinase and the coenzyme is NTP, which is converted into NDP.

When enzyme system 1 is the system in which the enzyme is NDP-dependent hexokinase and the coenzyme is NDP which is converted into NMP, NDP is consumed according to the glucose concentration, but an equal amount of NDP to that consumed is formed from NTP by the action of 6-phosphofructokinase, whereby the NDP concentration can be kept constant. Thus, the NDP concentration in the reaction system is not subject to variation due to the change in glucose concentration in a sample.

In the practice of the present invention, elimination of glucose is carried out by adding to a sample containing glucose (a) NDP, NTP, NDP-dependent hexokinase, phosphohexose isomerase and 6-phosphofructokinase, or (b) one member selected from the group consisting of NTP-dependent hexokinase and NTP-dependent glucokinase, NTP, phosphohexose isomerase and 6-phosphofructokinase, and subjecting the mixture to reaction at 10–50° C. for 1–30 minutes, preferably 2–10 minutes, if necessary in the presence of an aqueous medium, an enzyme activity moderator, an activator, a preservative, a stabilizer, a surfactant, a chromogen, an electron acceptor, a tetrazolium salt, an additional enzyme, a substrate for said enzyme, a coenzyme, etc.

The concentration of NDP-dependent hexokinase, NTP-dependent hexokinase and NTP-dependent glucokinase is preferably 0.1–100 U/ml, more preferably 0.5–50 U/ml, and most preferably 1–50 U/ml.

The concentration of phosphohexose isomerase is preferably 0.1–100 U/ml, more preferably 0.5–50 U/ml, and most preferably 5–50 U/ml.

The concentration of 6-phosphofructokinase is preferably 0. 1–100 U/ml, more preferably 0.5–50 U/ml, and most preferably 5–50 U/ml.

All of the above enzymes are commercially available and easily acquirable. For example, NDP-dependent hexokinase enzymes derived from *Thermococcus litoralis* and *Pyrococcus furiosus* are easily acquirable from Asahi Chemical Industry Co., Ltd., and NTP-dependent hexokinase enzymes derived from microorganisms of the genera. Saccharomyces, Kluyveromyces, Bacillus, etc. are easily acquirable from Oriental Yeast Co., Ltd., Toyobo Co., Ltd., Boehringer Mannheim GmbH, Asahi Chemical Industry Co., Ltd., etc. NTP-dependent glucokinase enzymes derived from microorganisms of the genera *Zymomonas, Bacillus,* etc. are easily acquirable from Unitika Ltd., etc. Phosphohexose isomerase derived from *Bacillus stearothermophilus* is available from Unitika Ltd. and 6-phosphofructokinase derived from *Bacillus stearothermophilus* is also available from Unitika Ltd.

The concentration of NDP and NTP is preferably 0.01–100 mM, more preferably 0.1–50 mM, and most preferably 1–10 mM. Examples of the activators include inorganic salts such as magnesium sulfate and magnesium chloride. The concentration of the inorganic salt is preferably 0.001–10 mg/ml, more preferably 0.01–5 mg/ml, and most preferably 0.1–2 mg/ml.

After glucose in a sample is eliminated by the above-described reaction, a reaction is carried out in the presence of a reagent necessary for the determination of an analyte in the sample and the amount of a substance formed or consumed by the reaction is measured, whereby the analyte can be determined. There is no specific restriction as to the reagent necessary for the determination, but it is appropriate to use a reagent containing an enzyme acting on the analyte or a substance reacting with the analyte, preferably, a reagent containing an enzyme acting on the analyte.

In cases where the enzyme acting on the analyte acts also on glucose and the reaction catalyzed by the enzyme is subject to the influence of the NDP concentration, it is preferred to eliminate glucose by using system (a) above in which the enzyme is NDP-dependent hexokinase and the coenzyme is NDP which is converted into NMP.

Examples of such enzymes include nucleotidase, 6-phosphogluconate dehydrogenase, NDP pyrophosphatase, NDP glucose pyrophosphorylase, NDP-dependent hexokinase and 1,5-AG-6-phosphate dehydrogenase.

When the above enzyme system for glucose elimination is applied to the determination of 1,5-AG, the enzyme system simultaneously catalyzes the conversion of 1,5-AG into 1,5-AG-6-phosphate, and 1,5-AG in a sample can be determined by measuring the amount of 1,5-AG-6-phosphate formed.

For the determination of 1,5-AG, after glucose in a sample is eliminated by the above reaction, 1,5-AG-6-phosphate dehydrogenase is added to the sample in the presence of an oxidized coenzyme and a reaction is carried out at 10–50° C. for 1–30 minutes, preferably 2–10 minutes, if necessary in the presence of an aqueous medium, an enzyme activity moderator, an activator, a preservative, a stabilizer, a surfactant, a chromogen, an electron acceptor, a tetrazolium salt, an additional enzyme, a substrate for said enzyme, a coenzyme, etc. The concentration of 1,5-AG can be determined by directly determining the amount of the reduced coenzyme formed by the reaction, for example, by measuring the absorbance at 340 nm, or by converting the reduced coenzyme into another substance and then determining the amount of the substance.

Either the oxidized coenzyme or 1,5-AG-6-phosphate dehydrogenase used in the determination of 1,5-AG may be present in the step of glucose elimination, so far as it does not affect the reaction for eliminating glucose.

As the NDP-dependent hexokinase, any enzyme can be used which catalyzes the reaction for forming glucose-6- phosphate and NMP using glucose as the substrate and consuming NDP and also catalyzes the reaction for forming 1,5-AG-6-phosphate and NMP using 1,5-AG as the substrate and consuming NDP. Examples of suitable enzymes are the enzyme derived from a hyperthermophile, *Pyrococcus furiosus* DSM3638 (Japanese Published Unexamined Patent Application No. 234098/97) and the enzyme derived from *Thermococcus litoralis* (TLHK), which are acquirable from Asahi Chemical Industry Co., Ltd.

As the NTP-dependent hexokinase or NTP-dependent glucokinase, any enzyme can be used which catalyzes the reaction for forming glucose-6-phosphate and NDP using glucose as the substrate and consuming NTP and also catalyzes the reaction for forming 1,5-AG-6-phosphate and NDP using 1,5-AG as the substrate and consuming NTP. Examples of suitable enzymes are the enzymes described above.

As the 1,5-AG-6-phosphate dehydrogenase, any enzyme can be used which catalyzes the reaction for forming a compound represented by $C_6H_{11}O_8P_1$ and a reduced coenzyme from 1,5-AG-6-phosphate and an oxidized coenzyme.

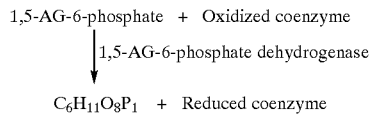

An example of 1,5-AG-6-phosphate dehydrogenase which is the enzyme catalyzing the above reaction is the enzyme derived from *Escherichia coli* DH1 (ATCC 33849). This enzyme can be prepared, for example, according to the method described in Japanese Published Unexamined Patent Application No. 84953/98.

The concentration of 1,5-AG-6-phosphate dehydrogenase in the reaction mixture is preferably 0.5–100 U/ml, more preferably 1–50 U/ml, and most preferably 2–40 U/ml. The concentration of the oxidized coenzyme in the reaction mixture is preferably 0.1–100 mM, more preferably 1–50 mM, and most preferably 2–20 mM.

The concentrations of NDP-dependent hexokinase, NTP-dependent hexokinase, NTP-dependent glucokinase, phosphohexose isomerase, 6-phosphofructokinase, NDP and NTP in the reaction mixture are the same as those described above for the reaction for glucose elimination.

Examples of the oxidized coenzyme include oxidized nicotinamide adenine dinucleotide (NAD), oxidized nicotinamide adenine dinucleotide phosphate (NADP), thio NAD and thio NADP.

Examples of NTP include adenosine triphosphate, guanosine triphosphate, cytidine triphosphate, thiamine triphosphate, uridine triphosphate and inosine triphosphate. Preferred is adenosine triphosphate.

Examples of NDP include adenosine diphosphate, guanosine diphosphate, cytidine diphosphate, thiamine diphosphate, uridine diphosphate and inosine diphosphate. Preferred is adenosine diphosphate.

The formed reduced coenzyme can be converted into another substance and determined with a high sensitivity. For example, as shown by the following equation, the reduced coenzyme is acted on by an electron acceptor in the presence of a tetrazolium salt and the formed formazan pigment is calorimetrically determined.

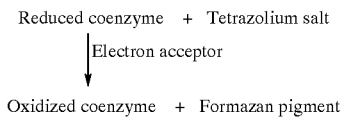

Tetrazolium salts useful in this method include indonitro tetrazolium (INT), nitro blue tetrazolium (NBT), 2-(4-iodophenyl)-3-(4-nitrophenyl)-5-(2,4-disulfonyl) -2H-tetrazoliummonosodiumsalt (hereinafter referred to as WST-1), 2-(4-iodophenyl)-3-(2,4-dinitrophenyl)-5-(2,4-disulfenyl)-2H-tetrazolium monosodium salt (hereinafter referred to as WST-3), 3,3'-[3,3'-dimethoxy-(1,1'-biphenyl)-4,4'-diyl]-bis[2-(4-nitrophenyl)-5-phenyl-2H tetrazolium chloride] (NTB) and 3-(4,5-dimethylthiazole-2-phenyl)-5-(3-carboxymethoxyphenyl)-2-(4-sulfophenyl)-2H-tetrazolium salt (MTS).

Tetrazolium salts which are used as chromogens can also be used. As the tetrazolium salt is used for the enhancement of sensitivity, those having high molecular extinction coefficient are preferred. Further, considering that the method will be applied usually to clinical assays, those which are converted into water-soluble formazan pigments after reduction are preferred. Specifically, WST-1 and WST-3 are preferably used. The amount of the tetrazolium salt for clinical use is preferably 0.01–50 mM.

The initial concentration of the tetrazolium salt in the reaction mixture is 0.01–50 mM, preferably 0.05–10 mM.

As the electron acceptor, phenazine methosulfate, 1-methoxy-5-methylphenazine methosulfate, Meldola's Blue, diaphorase, etc. may be used. An example of the diaphorase is the enzyme derived from *Bacillus megaterium*, which is acquirable from Asahi Chemical Industry Co., Ltd. and Toyobo Co., Ltd.

The initial concentration of the electron acceptor in the reaction mixture is 0.01–50 mM, preferably 0.05–10 mM.

The reaction is carried out at 10–50° C. for 1–30 minutes, preferably 2–10 minutes. This reaction may be carried out after the completion of the above reaction for forming the reduced coenzyme, but is preferably carried out simultaneously with the above reaction.

Described below is another method for determining the formed reduced coenzyme via the conversion into another substance. In this method, as shown by the following equation, the reduced coenzyme is acted on by reduced coenzyme oxidase and peroxidase in the presence of a chromogen and the formed pigment is calorimetrically determined. As the chromogen, chromogens used in combination with 4-aminoantipyrine or the like may be used, but those which can be used alone to produce pigments are preferred.

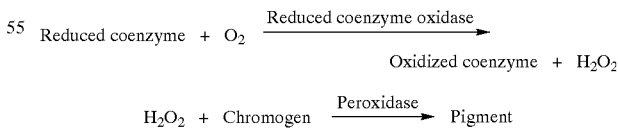

Examples of the chromogens which can be used alone are bis[3-bis(4-chlorophenyl)-methyl -4-dimethylaminophenyl] amine (BCMA), bis[3-bis(4-chlorophenyl)-methyl-4-carboxyethylaminophenyl]amine, 10-N-methylcarbamoyl-3,7-dimethylamino-10H-phenothiazine (MCDP) and 10-N-carboxymethylcarbamoyl-3,7-dimethylamino -10H-phenothiazine (CCAP).

Examples of the chromogens to be used in combination with 4-aminoantipyrine are N-ethyl-N-(3-methylphenyl)-N'-succinylethylenediamine (EMSE), N-ethyl-N-(2-hydroxy-3-sulfopropyl)-m-toluidine (TOOS) and N,N-bis(4-sulfobutyl)-m-toluidine disodium salt.

The reaction is carried out at 10–50° C. for 1–30 minutes, preferably 2–10 minutes. This reaction may be carried out after the completion of the above reaction for forming the reduced coenzyme, but is preferably carried out simultaneously with the above reaction.

As the aqueous medium, water-containing liquids such as buffers and physiological saline can be used. Buffers are preferably used.

Examples of the buffers are lactate buffer, citrate buffer, acetate buffer, succinate buffer, phthalate buffer, phosphate buffer, triethanolamine buffer, diethanolamine buffer, lysine buffer, barbital buffer, tris(hydroxymethyl)aminomethane buffer, imidazole buffer, malate buffer, oxalate buffer, glycine buffer, borate buffer, carbonate buffer and Good's buffer.

Examples of the enzyme activity moderators are metal chelating agents such as 1,10-phenanthroline, sugar alcohols such as mannitol and glycerol, metal ions such as magnesium, manganese, zinc and copper, and SH-blocking agents such as iodoacetic acid and iodoacetamide.

Examples of the enzyme stabilizers are metal chelating agents such as ethylenediaminetetraacetic acid, polysaccharides such as soluble starch and derivatives thereof, proteins such as albumin and globulin, water-soluble high-molecular weight compounds such as polyethylene glycol, and SH group-containing compounds such as phosphine and cysteine.

Examples of the surfactants are polyoxyethylene octylphenyl ether (Nonion HS-210, Kao Corporation), 3-[(3-chloramidepropyl)dimethylamino] propanesulfonic acid, Triton X-100 and sodium dodecyl sulfate.

An example of the preservatives is sodium azide.

As the additional enzyme, oxidized coenzyme oxidase, peroxidase, etc. can be used.

The reagent for the determination of 1,5-AG according to the present invention comprises (a) NDP, NTP, NDP-dependent hexokinase, phosphohexose isomerase, 6-phosphofructokinase, an oxidized coenzyme and 1,5-AG-6-phosphate dehydrogenase, or (b) one member selected from the group consisting of NTP-dependent hexokinase and NTP-dependent glucokinase, NTP, phosphohexose isomerase, 6-phosphofructokinase, an oxidized coenzyme and 1,5-AG-6-phosphate dehydrogenase, and may additionally contain, if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc.

Said reagent can be a kit for the determination of 1,5-AG which comprises 1) the first reagent comprising (a) NDP, NTP, NDP-dependent hexokinase, phosphohexose isomerase and 6-phosphofructokinase, or (b) one member selected from the group consisting of NTP-dependent hexokinase and NTP-dependent glucokinase, NTP, phosphohexose isomerase and 6-phosphofructokinase, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc., and 2) the second reagent comprising 1,5-AG-6-phosphate dehydrogenase and an oxidized coenzyme, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc. It is also possible to formulate the second reagent to contain either one of the 1,5-AG-6-phosphate dehydrogenase and the oxidized coenzyme and to formulate the first reagent to contain the other one.

The reagent for the elimination of glucose according to the present invention comprises NDP, NTP, NDP-dependent hexokinase, phosphohexose isomerase and 6-phosphofructokinase, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc.

The reagent for the determination of an analyte according to the present invention comprises NDP, NTP, NDP-dependent hexokinase, phosphohexose isomerase, 6-phosphofructokinase, and an enzyme acting on the analyte or a substance reacting with the analyte, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc.

Said reagent can be a kit which comprises 1) the first reagent comprising NDP, NTP, NDP-dependent hexokinase, phosphohexose isomerase and 6-phosphofructokinase, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc., and 2) the second reagent comprising an enzyme acting on the analyte or a substance reacting with the analyte, and if necessary, the above-mentioned buffer agent, enzyme activity moderator, activator, preservative, stabilizer, surfactant, chromogen, electron acceptor, tetrazolium salt, additional enzyme, substrate for said enzyme, coenzyme, etc.

Each of the reagents according to the present invention may be provided in the form of a freeze-dried preparation or in the form of a solution in an aqueous medium such as water.

Certain embodiments of the present invention are illustrated in the following examples.

EXAMPLE 1

A reagent for the elimination of glucose having the following composition was prepared.

| | |
|---|---|
| Tris-HCl buffer (pH 8.0) | 50 mM |
| Magnesium chloride | 1 mg/ml |
| ADP-dependent hexokinase (derived from *Thermococcus litoralis*, Asahi Chemical Industry Co., Ltd.) | 10 U/ml |
| Phosphohexose isomerase (derived from *Bacillus stearothermophilus*, Unitika Ltd.) | 40 U/ml |
| 6-Phosphofructokinase (derived from *Bacillus stearothermophilus*, Unitika Ltd.) | 30 U/ml |
| ADP (Oriental Yeast Co., Ltd.) | 3 mM |
| ATP (Sigma Chemical Co.) | 10 mM |

EXAMPLE 2

Reagents for the determination of 1,5-AG having the following composition were prepared.

| Reagent 1 | |
| --- | --- |
| Tris-HCl buffer (pH 8.5) | 50 mM |
| Magnesium chloride | 1 mg/ml |
| NADP (Sigma Chemical Co.) | 4 mM |
| ADP (Oriental Yeast Co., Ltd.) | 3 mM |
| ATP (Sigma Chemical Co.) | 10 mM |
| Phosphohexose isomerase (derived from *Bacillus stearothermophilus*, Unitika Ltd.) | 40 U/ml |
| 6-Phosphofructokinase (derived from *Bacillus stearothermophilus*, Unitika Ltd.) | 30 U/ml |
| Diaphorase (derived from *Bacillus megaterium*, Asahi Chemical Industry Co., Ltd.) | 10 U/ml |
| ADP-dependent hexokinase (derived from *Thermococcus litoralis*, Asahi Chemical Industry Co., Ltd.) | 10 U/ml |
| Reagent 2 | |
| Glycine-NaOH buffer (pH 10.0) | 200 mM |
| WST-1 (Dojindo Laboratories) | 0.5 mM |
| 1,5-AG-6-phosphate dehydrogenase (derived from *E. coli* DH1 (ATCC 33949), Asahi Chemical Industry Co., Ltd.) | 20 U/ml |

EXAMPLE 3

A standard solution of 1,5-AG (25 μg/ml) was diluted to prepare five solutions having different concentrations. To 0.075 ml of each of the solutions and purified water was added 2.25 ml of reagent 1 prepared in Example 2, followed by incubation at 37° C. for 5 minutes. After 0.75 ml of reagent 2 prepared in Example 2 was added to each mixture, the reaction was carried out for 5 minutes and the absorbance was measured at 438 nm. The obtained calibration curve is shown in FIG. 1.

EXAMPLE 4

The following experiment on glucose elimination was carried out to prove the utility of the method according to the invention. Reagent 1 prepared in Example 2 was poured into test tubes in 2.25 ml portions. To the test tubes were respectively added 0.075 ml each of (a) purified water, (b) a test solution containing 25 μg/ml 1,5-AG, (c) a test solution containing 2000 mg/dl glucose, and (d) a test solution containing 25 μg/ml 1,5-AG and 2000 mg/dl glucose, followed by incubation at 37° C. for 5 minutes. After 0.75 ml of reagent 2 prepared in Example 2 was added to each mixture, the reaction was carried out for 5 minutes and the absorbance was measured at 438 nm. The results are shown in Table 1.

TABLE 1

| Test solution | Measurement result |
| --- | --- |
| (a) Purified water (blank) | 0.096 Abs |
| (b) 1,5-AG 25 μg/ml | 0.230 Abs |
| (c) Glucose 2000 mg/dl | 0.096 Abs |
| (d) 1,5-AG + glucose | 0.226 Abs |

As shown in Table 1, the value of (c) exactly agreed with that of (a), indicating that 2000 mg/dl glucose contained in test solution (c) was completely eliminated by the method of the invention. Further, the value of (b) closely agreed with that of (d). The utility of the method according to the invention was thus proved.

EXAMPLE 5

Determination of 1,5-AG was carried out on 50 serum samples to examine the correlation between the method according to the invention and a known method.

(a) To 2.25 ml of reagent 1 prepared in Example 2 was added 0.075 ml of each sample, followed by incubation at 37° C for 5 minutes. After 0.75 ml of reagent 2 prepared in Example 2 was added to the mixture, the reaction was carried out for 5 minutes and the absorbance was measured at 438 nm. The 1,5-AG concentration in the sample was calculated from the absorbance according to the equation obtained from the calibration curve of Example 1 shown in FIG. 1.

(b) Measurement was made on the 50 serum samples using an approved reagent for in vitro diagnostic use, Lana 1,5-AGAutoII (Nippon Kayaku Co., Ltd., Approval No. (08AM) 0112) according to its "measurement procedure" and the 1,5-AG concentration was calculated according to its "method of calculating 1,5-AG concentration".

The 1,5-AG concentration determined in (a) was plotted as ordinate and that determined in (b) as abscissa. The result is shown in FIG. 2.

Figure 2:
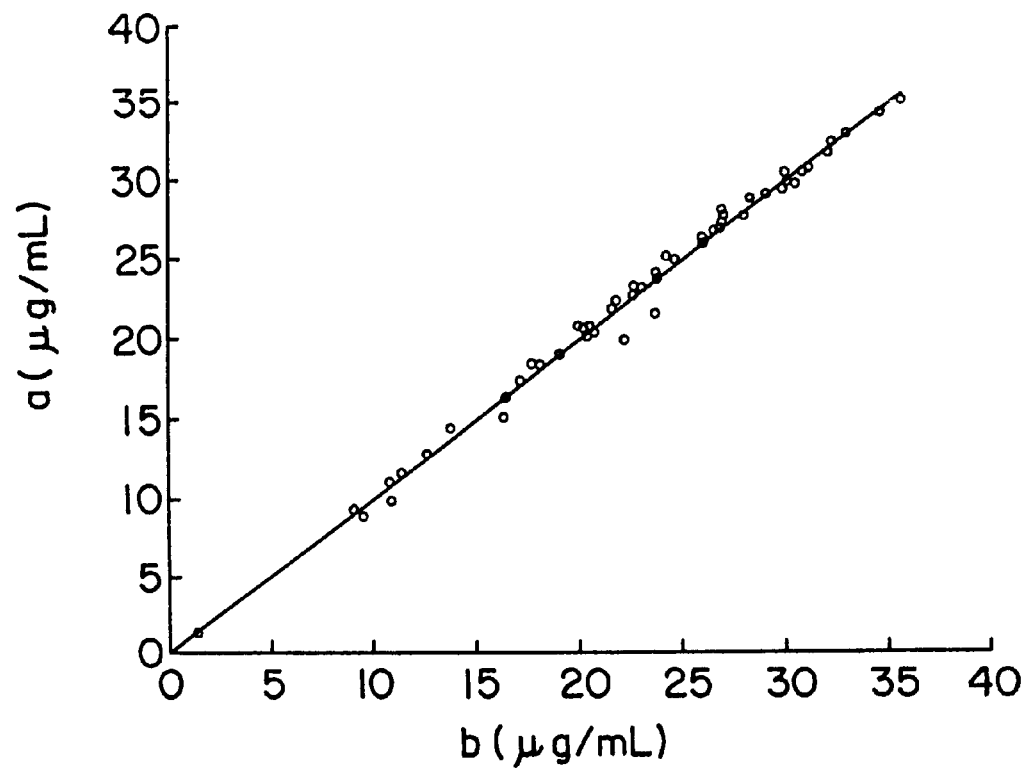
FIG. 2 is a graph showing the correlation between the 1,5-AG concentration determined by the method of the invention (a: ordinate) and the 1,5-AG concentration determined by the control method (Lana 1,5-AG Auto) (b: abscissa).

The result in FIG. 2 shows a good correlation between the data with the correlation coefficient r=0.9966 and the regression equation y=0.9839x+0.0576.

EXAMPLE 6

Reagents were prepared in the same manner as in Example 2, except that the ADP concentration in the first reagent was varied as indicated in Table 2 and Triton X-100 was added to the composition of reagent 2 at a concentration of 0.4%.

Test solutions containing 25 μg/ml 1,5-AG and glucose at the concentrations indicated in Table 2 were prepared.

Determination of 1,5-AG was carried out on the test solutions in the same manner as in Example 3. The results are shown in Table 2.

TABLE 2

| Glucose concentration | ADP concentration (mM) | | | | | | | |
| --- | --- | --- | --- | --- | --- | --- | --- | --- |
| (mg/dl) | 0.5 | 1 | 2 | 3 | 4 | 5 | 6 | 10 |
| 0 | 25.2 | 25.1 | 25.0 | 25.0 | 25.2 | 25.1 | 25.1 | 25.0 |
| 400 | 25.0 | 25.1 | 25.1 | 25.0 | 25.1 | 25.1 | 25.1 | 25.0 |
| 800 | 24.9 | 25.2 | 25.0 | 25.0 | 25.2 | 25.0 | 25.1 | 25.1 |
| 1200 | 24.8 | 25.0 | 24.9 | 25.1 | 25.1 | 25.1 | 25.3 | 25.2 |
| 1600 | 24.8 | 25.0 | 24.8 | 25.0 | 25.1 | 25.2 | 25.2 | 25.3 |
| 2000 | 24.8 | 25.1 | 25.0 | 25.1 | 25.2 | 25.3 | 25.3 | 25.6 |

It was demonstrated that 1,5-AG in samples can be accurately determined by employing the above method for glucose elimination using ADP-dependent hexokinase, regardless of ADP concentration in the reagents and glucose concentration in the samples.

EXAMPLE 7

Reagents for the determination of 1,5-AG having the following composition were prepared.

| Reagent 1 | |
| --- | --- |
| Tris-HCl buffer (pH 8.0) | 50 mM |
| Magnesium chloride | 1 mg/ml |
| NADP (Sigma Chemical Co.) | 4 mM |
| ATP (Sigma Chemical Co.) | 10 mM |
| Phosphohexose isomerase (derived from *Bacillus stearothermophilus*, Unitika Ltd.) | 40 U/ml |

-continued

| | |
|---|---|
| 6-Phosphofructokinase (derived from *Bacillus stearothermophilus*, Unitika Ltd.) | 30 U/ml |
| Diaphorase (derived from *Bacillus megaterium*, Asahi Chemical Industry Co., Ltd.) | 10 U/ml |
| ATP-dependent hexokinase (derived from yeast, Oriental Yeast Co., Ltd.) | 100 U/ml |
| Reagent 2 | |
| Glycine-NaOH buffer (pH 10.0) | 200 mM |
| WST-1 (Dojindo Laboratories) | 0.5 mM |
| 1,5-AG-6-phosphate dehydrogenase (derived from *E. coli* DH1 (ATCC 33849), Asahi Chemical Industry Co., Ltd.) | 20 U/ml |

EXAMPLE 8

Figure 3:
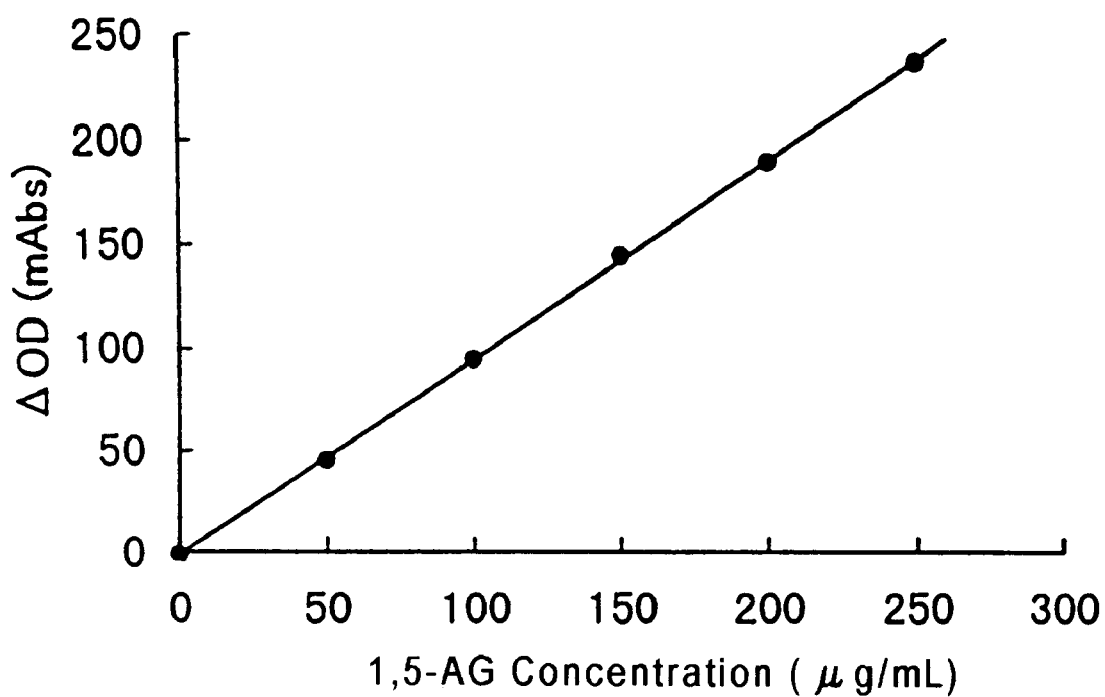
FIG. 3 shows a calibration curve for 1,5-AG.

Standard solutions respectively containing 50, 100, 150, 200 and 250 µg/ml 1,5-AG were prepared. To 0.075 ml of each of the standard solutions and purified water was added 2.25 ml of reagent 1 prepared in Example 7, followed by incubation at 37° C. for 5 minutes. After 0.75 ml of reagent 2 prepared in Example 7 was added to each mixture, the reaction was carried out for 5 minutes and the absorbance was measured at 438 nm. The obtained calibration curve is shown in FIG. 3.

EXAMPLE 9

The following experiment on glucose elimination was carried out to prove the utility of the method according to the invention. Reagent 1 prepared in Example 7 was poured into test tubes in 2.25 ml portions. To the test tubes were respectively added 0.075 ml each of (a) purified water, (b) a test solution containing 250 µg/ml 1,5-AG, (c) a test solution containing 100 mg/dl glucose, and (d) a test solution containing 250 µg/ml 1,5-AG and 100 mg/dl glucose, followed by incubation at 37° C. for 5 minutes. After 0.75 ml of reagent 2 prepared in Example 7 was added to each mixture, the reaction was carried out for 5minutes and the absorbance was measured at 438 nm. The results are shown in Table 3.

TABLE 3

| Test solution | Measurement result |
|---|---|
| (a) Purified water (blank) | 0.280 Abs |
| (b) 1,5-AG 250 ug/ml | 0.440 Abs |
| (c) Glucose 100 mg/dl | 0.279 Abs |
| (d) 1,5-AG + glucose | 0.441 Abs |

As shown in Table 3, the value of (c) closely agreed with that of (a), indicating that 100 mg/dl glucose contained in test solution (c) was completely eliminated by the method of the invention. Further, the value of (b) closely agreed with that of (d). The utility of the method according to the invention was thus proved.

What is claimed is:

1. A method for determining 1,5-anhydroglucitol in a sample containing glucose, which comprises:
 contacting the sample with adenosine diphosphate, adenosine triphosphate, adenosine diphosphate-dependent hexokinase, phosphohexose isomerase and 6-phosphofructokinase to form fructose-1,6-diphosphate and 1,5-anhydroglucitol-6-phosphate;
 dehydrogenating the 1,5-anhydroglucitol-6-phosphate by the action of 1,5-anhydroglucitol-6-phosphate dehydrogenase in the presence of an oxidized coenzyme; and
 measuring the amount of reduced coenzyme formed by the dehydrogenation reaction.

2. The method according to claim 1, wherein said coenzyme is nicotinamide adenine dinucleotide phosphate.

3. The method according to claim 1 or 2, wherein said measurement of the amount of the reduced coenzyme is carried out by colorimetry of a pigment formed from a tetrazolium salt.

4. A reagent for the determination of 1,5-anhydroglucitol, comprising adenosine diphosphate, adenosine triphosphate, adenosine diphosphate-dependent hexokinase, phosphohexose isomerase, 6-phosphofructokinase, an oxidized coenzyme and 1,5-anhydroglucitol-6-phosphate dehydrogenase.

5. The reagent according to claim 4, wherein said coenzyme is nicotinamide adenine dinucleotide phosphate.

6. The reagent according to claim 4 or 5, further comprising a tetrazolium salt and an electron acceptor.

7. A reagent kit for the determination of 1,5-anhydrogluitol, said reagent kit comprising (i) a reagent comprising adenosine diphosphate, adenosine triphosphate, adenosine diphosphate-dependent hexokinase, phosphohexose isomerase and 6-phosphofructokinase and (ii) a second reagent comprising oxidized nicotinamide adenine dinucleotide phosphate and 1,5-anhydroglucitol-6-phosphate dehydrogenase.

8. A method for eliminating glucose in a sample, which comprises converting glucose in the sample into fructose-1,6-diphosphate by the action of adenosine diphosphate-dependent hexokinase, phosphohexose isomerase and 6-phosphofructokinase in the presence of adenosine diphosphate and adenosine triphosphate.

9. A reagent for the elimination of glucose, comprising adenosine diphosphate, adenosine triphosphate, adenosine diphosphate-dependent hexokinase, phosphohexose isomerase and 6-phosphofructokinase.

10. A method for determining an analyte in a sample containing glucose, which comprises:
 converting glucose in the sample into fructose-1,6-diphosphate by the action of adenosine diphosphate-dependent hexokinase, phosphohexose isomerase and 6-phosphofructokinase in the presence of adenosine diphosphate, adenosine triphosphate; and
 determining the analyte in the sample by using a chemical or enzymatic reaction.

11. A reagent for the determination of an analyte, comprising adenosine diphosphate, adenosine triphosphate, adenosine diphosphate-dependent hexokinase, phosphohexose isomerase and 6-phosphofructokinase, and an enzyme acting on the analyte or a substance reacting with the analyte.

12. A reagent kit for the determination of an analyte, comprising (i) a reagent comprising adenosine diphosphate, adenosine triphosphate, adenosine diphosphate-dependent hexokinase, phosphohexose isomerase and 6-phosphofructokinase, and (ii) a second reagent comprising an enzyme acting on the analyte or a substance reacting with the analyte.

13. A reagent kit for the determination of 1,5-AG, comprising:
 a first reagent comprising (a) NDP, NTP, NDP-dependent hexokinase, phosphohexose isomerase and 6-phosphofructokinase, and (b) an oxidized coenzyme; and
 a second reagent comprising 1,5-AG-6-phosphate dehydrogenase.

14. The reagent kit according to claim 13, wherein said NDP, NTP, NDP-dependent hexokinase are ADP, ATP, and ADP-dependent hexokinase, respectively.

15. The reagent kit according to claim 13 or 14, wherein said first reagent further comprises an electron carrier and magnesium salt, and said second reagent further comprises tetrazolium salt.

16. A reagent kit for the determination of 1,5-AG, comprising:

a first reagent comprising (a) one member selected from the group consisting of NTP-dependent hexokinase and NTP-dependent glucokinase, NTP, phosphohexose isomerase and 6-phosphofrutokinase, and (b) an oxidized coenzyme; and a second reagent comprising 1,5-AG-6-phosphate dehydrogenase.

17. The reagent kit according to claim 16, wherein said NTP-dependent hexokinase and NTP-dependent glucokinase are ATP-dependent hexokinase and ATP-dependent glucokinase, respectively.

18. The reagent kit according to claim 16 or 17, wherein said first reagent further comprises an electron carrier and magnesium salt, and said second reagent further comprises tetrazolium salt.

* * * * *

UNITED STATES PATENT AND TRADEMARK OFFICE
CERTIFICATE OF CORRECTION

PATENT NO. : 6,448,029 B1
DATED : September 10, 2002
INVENTOR(S) : Sakae Tazoe et al.

It is certified that error appears in the above-identified patent and that said Letters Patent is hereby corrected as shown below:

Title page,
Item [30], Foreign Application Priority Data,
"Dec. 7, 1999" should read -- Dec. 11, 1998 --.
Item [56], U.S. PATENT DOCUMENTS, insert:
-- 5,468,621   11/1995   Kojima et al. ............ 435/25
5,486,458   1/1996   Kojima et al. ............ 435/14 --.
FOREIGN PATENT DOCUMENTS , insert
-- JP   6-237795   8/1994
JP   10-33195   2/1998
EP   0 846 773   6/1998
EP   825 258   2/1998 --.

Column 3,
Line 46, "nucleosidediphos-" should read -- nucleoside diphos- --.

Column 6,
Line 4, "genera." should read -- genera --;
Line 43, "detem-" should read -- determ --;
Line 46, "ina" should read -- in a --.

Column 8,
Line 11, "tetrazoliummonosodiumsalt" should read -- tetrazolium monosodium salt --.

Column 11,
Line 46, "5minutesandtheabsorbancewasmeasuredat438nm." should read -- 5 minutes and the absorbance was measured at 438 nm. --.

Column 13,
Line 38, "5minutes" should read -- 5 minutes --.

UNITED STATES PATENT AND TRADEMARK OFFICE
CERTIFICATE OF CORRECTION

PATENT NO.    : 6,448,029 B1
DATED         : September 10, 2002
INVENTOR(S)   : Sakae Tazoe et al.

It is certified that error appears in the above-identified patent and that said Letters Patent is hereby corrected as shown below:

Column 14,
Line 18, "anhydrogluitol," should read -- anhydroglucitol, --;
Line 40, "diphosphate," should read -- diphosphate and --.

Signed and Sealed this

Fifteenth Day of April, 2003

JAMES E. ROGAN
*Director of the United States Patent and Trademark Office*